(12) United States Patent
Toriyama et al.

(10) Patent No.: US 6,734,677 B2
(45) Date of Patent: May 11, 2004

(54) DEVICE AND METHOD FOR DETECTING ENGINE COMBUSTION CONDITION

(75) Inventors: Makoto Toriyama, Chiryu (JP); Tohru Yoshinaga, Okazaki (JP); Hiroshi Yorita, Kariya (JP)

(73) Assignee: Denso Corporation, Kariya (JP)

( * ) Notice: Subject to any disclaimer, the term of this patent is extended or adjusted under 35 U.S.C. 154(b) by 58 days.

(21) Appl. No.: 10/269,948

(22) Filed: Oct. 15, 2002

(65) Prior Publication Data

US 2003/0076111 A1 Apr. 24, 2003

(30) Foreign Application Priority Data

Oct. 19, 2001 (JP) .......................... 2001-321749

(51) Int. Cl.$^7$ ................................. F02P 17/00
(52) U.S. Cl. ..................... 324/399; 324/380; 324/459
(58) Field of Search ............... 73/35.08, 116; 123/594, 606, 625; 324/378, 380, 388, 393, 399, 459; 340/629

(56) References Cited

U.S. PATENT DOCUMENTS

| | | | | |
|---|---|---|---|---|
| 6,104,195 A | * | 8/2000 | Yoshinaga et al. | .......... 324/459 |
| 6,118,276 A | * | 9/2000 | Nakata et al. | .............. 324/464 |
| 6,360,587 B1 | * | 3/2002 | Noel | ......................... 73/35.08 |
| 6,512,375 B1 | * | 1/2003 | Yamada et al. | ............. 324/399 |
| 6,557,537 B2 | * | 5/2003 | Ikeda et al. | ................. 123/606 |
| 6,614,230 B2 | * | 9/2003 | Raichle et al. | ............. 324/399 |
| 6,653,840 B2 | * | 11/2003 | Yorita et al. | ................ 324/380 |

\* cited by examiner

*Primary Examiner*—N. Le
*Assistant Examiner*—Walter Benson
(74) *Attorney, Agent, or Firm*—Nixon & Vanderhye P.C.

(57) ABSTRACT

A combustion condition detecting device detects combustion ions between opposing electrodes in a combustion chamber by ion current flowing between the electrodes in response to a.c. current voltage applied between the electrodes. A low pass filter for eliminating current components having high order frequencies of the a.c. voltage is disposed in a primary side of the transformer so that a waveform of the a.c. voltage approximates a sine wave. Thus, detection accuracy of the combustion ions is prevented from being affected by variation of capacitive current included in the current flowing between the electrodes, wherein the variation of the capacitive current is caused by distortion of the waveform of the a.c. voltage.

5 Claims, 3 Drawing Sheets

DEVICE AND METHOD FOR DETECTING ENGINE COMBUSTION CONDITION

CROSS REFERENCE TO RELATED APPLICATION

This application is based on and incorporates herein by reference Japanese Patent Application No. 2001-321749 filed on Oct. 19, 2001.

FIELD OF THE INVENTION

The present invention relates to a combustion condition detecting device for detecting combustion condition in an internal combustion engine.

BACKGROUND OF THE INVENTION

A known combustion condition detecting device for detecting combustion condition in an internal combustion engine has a pair of opposing electrodes of a spark plug, the electrodes being connected with a current source. The combustion condition detecting device detects intensity of combustion by detecting a combustion ion current that flows between the opposing electrodes in correspondence with quantity of combustion ions existing between the opposing electrodes. This scheme is based on the fact that the quantity of the combustion ions generated in the combustion chamber changes in correspondence with the combustion condition, such as the intensity of the combustion. Thus, the combustion condition detecting device detects the combustion condition, especially an abnormal combustion condition, to control timing of discharging spark, air-fuel ratio and the like to retain favorable combustion condition, aiming at improving fuel consumption and cleaning up exhaust emissions.

U.S. Pat. No. 6,104,195 (Japanese Patent Laid-Open Publication No. 9-25867) discloses a combustion condition detecting device that applies an alternating current voltage to a pair of opposing electrodes through a transformer. Thus, combustion ions are prevented from being attracted and eliminated by the opposing electrodes, and the reduction of the detection outputs is prevented.

In this combustion condition detecting device, when the alternating current voltage is applied between the opposing electrodes, the opposing electrodes operate as a capacitor and conduct a current, which is referred to as a capacitive current hereafter. In order to inhibit the effect caused by the capacitive current, the device employs the following schemes. That is, the combustion condition detecting device monitors the fluctuation of quantity of the combustion ions by sampling current values at given phases corresponding to the alternating current voltage, as the capacitive current changes in a predetermined cycle corresponding to the alternating current voltage. Alternatively, the combustion condition detecting device monitors the fluctuation of the quantity of the combustion ions by detecting the phase differences between given phases corresponding to the alternating current voltage and phases in which the current value becomes a predetermined value.

However, the waveform of the capacitive current varies in correspondence with a degree of distortion of the waveform of the alternating current voltage applied to the opposing electrodes, causing errors in detection. In order to reduce the variations of the waveform of the capacitive current, correction may be made to the outputs of the combustion condition detecting device. However, the distortion of the waveform of the applied voltage varies due to the changes with time in characteristics of the parts constructing the combustion condition detecting device. Therefore, correction of the outputs is not capable of solving the problem fully. Alternatively, if the distortion of the waveform of the applied voltage varies due to individual differences of the parts constructing the combustion condition detecting device, it may be applicable to adjust every combustion condition detecting device individually. However, if the waveform of the applied voltage has some types of distortions, complicated adjustments between the sampled values or the detected phases and the quantity of the combustion ions are needed. Therefore, the approach of adjusting every combustion condition detecting device individually is not suitable for a mass production.

SUMMARY OF THE INVENTION

It is therefore an object of the present invention to provide a combustion condition detecting device and method for detecting combustion condition in an internal combustion engine with a high accuracy in detecting combustion ions.

According to an aspect of the present invention, a combustion condition detecting device for detecting combustion condition in a combustion chamber of an internal combustion engine has a pair of opposing electrodes disposed in the combustion chamber. The opposing electrodes are applied with an alternating current voltage through a transformer. The combustion condition detecting device detects quantity of combustion ions existing between the opposing electrodes by a current signal that represents magnitude of a current flowing between the opposing electrodes. The combustion condition detecting device has a low pass filter disposed in the primary side of the transformer. The low pass filter eliminates current components having high order frequencies of the alternating current voltage.

Since the low pass filter eliminates the current components having high order frequencies of the alternating current voltage that is outputted through the transformer and is applied to the opposing electrodes, distortion of a waveform of the alternating current voltage is reduced. As a result, the quantity of the combustion ions is detected precisely, regardless of the changes with time in the characteristics and the individual differences of the parts constructing the combustion condition detecting device.

According to another aspect of the present invention, the low pass filter is constructed by a capacitor. The capacitor discharges the current components having high order frequencies of the alternating current voltage to a grounding side.

BRIEF DESCRIPTION OF THE DRAWINGS

The above and other objects, features and advantages of the present invention will become more apparent from the following detailed description made with reference to the accompanying drawings. In the drawings.

DETAILED DESCRIPTION OF THE REFERRED EMBODIMENT

Figure 1:
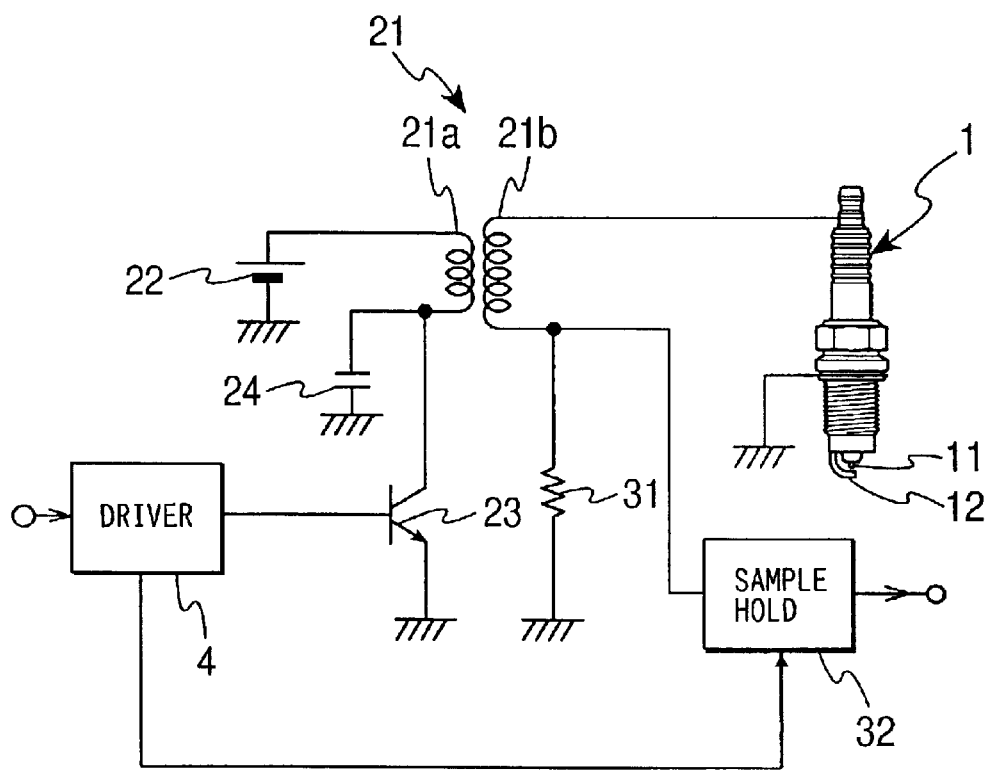
FIG. 1 is a schematic circuit diagram of a combustion condition detecting device according to an embodiment of the present invention.

As shown in FIG. 1, a spark plug 1 disposed in a combustion chamber of an internal combustion engine has a pair of opposing electrodes 11, 12 for discharging spark. One electrode 11 is connected with one terminal of a secondary winding 21b of a transformer (ignition coil) 21 and the other electrode 12 is grounded.

One terminal of a primary winding 21a of the transformer 21 is connected with a battery 22 and the other terminal of the primary winding 21a is connected with a collector of a switching transistor 23 that turns on and off a voltage applied by the battery 22.

The other terminal of the primary winding 21a is connected with a capacitor 24, which is in parallel with the switching transistor 23.

An ignition and ion-detection driver 4 comprises a logic operation circuit, an oscillator and the like. The ignition and ion-detection driver 4 outputs a first control signal (FIG. 2) and a second control signal in compliance with commands inputted by an engine control ECU (not shown). The ignition and ion-detection driver 4 inputs the first control signal to the base of the switching transistor 23.

Figure 2:
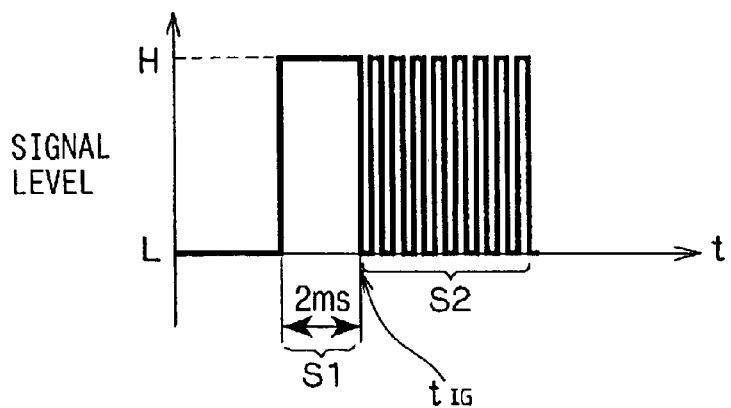
FIG. 2 is a schematic diagram showing control signals of the combustion condition detecting device according to the embodiment of the present invention.

As shown in the part S1 in FIG. 2, the first control signal rises to level "H" before the ignition timing $t_{IG}$, retains the level "H" for 2 milliseconds, and falls to level "L" at the ignition timing $t_{IG}$. Next, the first control signal becomes a series of pulse signals that change between the level "H" and the level "L" alternately at a frequency of 30 kHz as shown in another part S2 in FIG. 2. The first control signal denoted by the part S1 in FIG. 2 is referred to as an ignition control signal hereafter. The first control signal denoted by the part S2 in FIG. 2 is referred to as an ion detection control signal hereafter.

A detection resistor 31 for detecting the current flowing between the opposing electrodes 11, 12 is disposed between the other terminal of the secondary winding 21b of the transformer 21 and the electrode 12. The secondary winding 21b side of the detection resistor 31 is connected with a sample-and-hold circuit 32. A potential difference between both terminals of the detection resistor 31 is inputted to the sample-and-hold circuit 32 as a current signal corresponding to the current flowing between the opposing electrodes 11, 12.

The sample-and-hold circuit 32 receives the second control signal from the ignition and ion-detection driver 4 and samples the current signal from the detection resistor 31. The second signal is a series of pulse signals with an equivalent content with the ion detection control signal of the first signal. The sample-and-hold circuit 32 performs a sampling of the current signals at a frequency of 30 kHz in compliance with the second control signal. The second signal is outputted with a given phase difference relative to the ion detection control signal. The phase difference between the ion detection control signal and the second signal is determined so that the capacitive current value equals to "0" at the sampling timing, for instance. The phase difference is obtained in advance by experiments and the like.

Operations of the combustion condition detecting device will be explained below.

The combustion condition detecting device also operates as a means for igniting the mixed gas of the air and the fuel introduced into the combustion chamber. When the switching transistor 23 is turned on by the ignition control signal (part S1), the transformer 21 operating as an ignition coil is charged with ignition energy supplied by the battery 22. 2 milliseconds after the switching transistor 23 is turned on, the ignition control signal changes from the level "H" to "L" and the switching transistor 23 is turned off. Accordingly, a high voltage is applied between the electrodes 11, 12 by electromagnetic induction and a spark is discharged between the opposing electrodes 11, 12 to ignite the mixed gas.

Then, the ion detection control signal (part S2) is outputted, and the voltage between the terminals of the battery 22 is applied to the primary winding 21a of the transformer 21 intermittently in the cycle of the ion detection control signal. Thus, alternating high voltage having a frequency corresponding to the ion detection control signal is induced across the secondary winding 21b of the transformer 21 by electromagnetic induction. The alternating current voltage is applied between the opposing electrodes 11, 12 of the spark plug 1.

The alternating current voltage applied between the electrodes 11, 12 causes a current therebetween. The current is a summation of the capacitive current and a combustion ion current. The combustion ion current changes due to the changes of conductance between the opposing electrodes 11, 12, wherein the conductance changes in correspondence with the quantity of the combustion ions existing between the opposing electrodes 11, 12. The capacitive current is proportional to the alternating current voltage differentiated by time and does not depend on the quantity of the combustion ions.

The second control signal inputted to the sample-and-hold circuit 32 has the same frequency as the ion detection control signal and has a constant and predetermined phase difference relative to the ion detection control signal. Therefore, among the current signal inputted at a sampling cycle to the sample-and-hold circuit 32, the capacitive current has a constant value if the distortion of the waveform of the alternating current voltage applied to the opposing electrodes 11, 12 is neglected. Accordingly, the sampled current signal increases and decreases basically due to the quantity of the combustion ions alone. The capacitive current has a large value when the quantity of the combustion ions is large, and a small value when the quantity of the combustion ions is small.

Then, signals outputted by the sample-and-hold circuit 32 are inputted to a controlling part constructed by a microcomputer and the like, and is used for determining a combustion condition.

The voltage that is outputted by the secondary winding 21b and is applied between the opposing electrodes 11, 12 is referred to as a secondary side voltage hereafter. On the other hand, a frequency equal to that of the ion detection control signal is referred to as an applied frequency. If the secondary side voltage has a sinusoidal waveform of which frequency is equal to the applied frequency, the capacitive current is equal to "0" when the current is sampled at the phases deviating from that of the secondary side voltage by 90°. However, if the waveform of the voltage is distorted and the capacitor 24 is not provided, the capacitive current is not necessarily equal to "0" when the current is sampled at the phases deviating from that of the secondary side voltage by 90°. If the distortion of the waveform of the voltage is caused by the characteristics of parts constructing the device, the distortion may be regarded as components with high order frequencies. Accordingly, the capacitive current includes current components with high order frequencies that are integral multiples of the frequency of the ion detection control signal, in addition to a sinusoidal component that increases and decreases in the applied frequency. The sinusoidal component is referred to as an applied frequency component hereafter.

Figure 3:
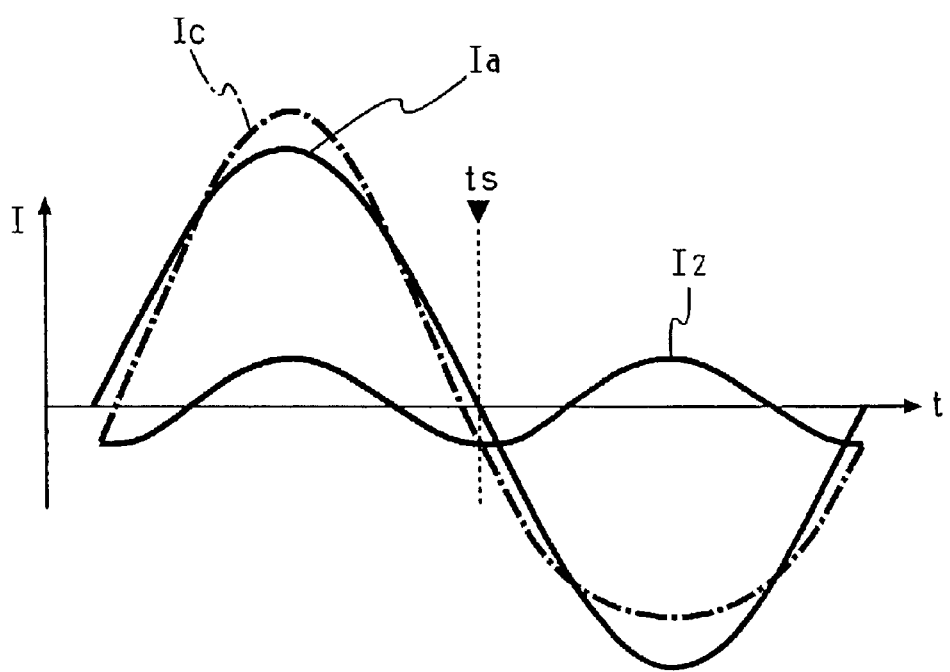
FIG. 3 is a schematic diagram showing an operation of the combustion condition detecting device according to the embodiment of the present invention.

FIG. 3 is a diagram illustrating the current that flows through the secondary winding 21b of the transformer 21 when the combustion ion is null, wherein the current is referred to as a secondary side current hereafter. Since the quantity of combustion ion is equal to "0", the secondary side current is equal to the capacitive current. In FIG. 3, $I_c$ represents a waveform of the capacitive current, which includes current components with high order frequencies as distortions. In FIG. 3 again, $I_a$ represents a waveform of the applied frequency component and $I_2$ represents another current component with the second order frequency as a high order frequency. If the secondary side voltage has a sinusoidal waveform, the capacitive current $I_c$ should be equal to "0" at the sampling timing $t_s$ shown in FIG. 3. However, the secondary side current, the capacitive current $I_c$, has a negative value because the secondary side current includes the current component $I_2$ with a high order frequency. The detection error of the combustion ions due to the deviation of the capacitive current value $I_c$ at the sampling timing $t_s$ is not fully complied with by a means such as an offset correction.

On the other hand, the combustion condition detecting device according to the embodiment includes the capacitor 24. Therefore, when the switching transistor 23 is turned on, a gradually increasing current flows through the primary winding 21a. Conversely, when the switching transistor 23 is turned off, a gradually decreasing current flows through the primary winding 21a, the current being caused by the passage between the primary winding 21a and the capacitor 24. Accordingly, the waveform of the capacitive current approximates a sine wave. That is, the capacitor 24 discharges the current components with high order frequencies to the ground side. Accordingly, the waveform of the alternating current voltage applied between the electrodes 11, 12 approximates a sinusoidal waveform of which components with high order frequencies are reduced. As a result, phases in which the capacitive current is equal to a predetermined value, "0" for instance, are settled and the detection accuracy of the quantity of the combustion ions is improved.

The capacitance of the capacitor 24 is large enough to inhibit the current components with high order frequencies, in consideration of the reactance of the capacitor 24 in a range of the high order frequencies.

Figure 4A:
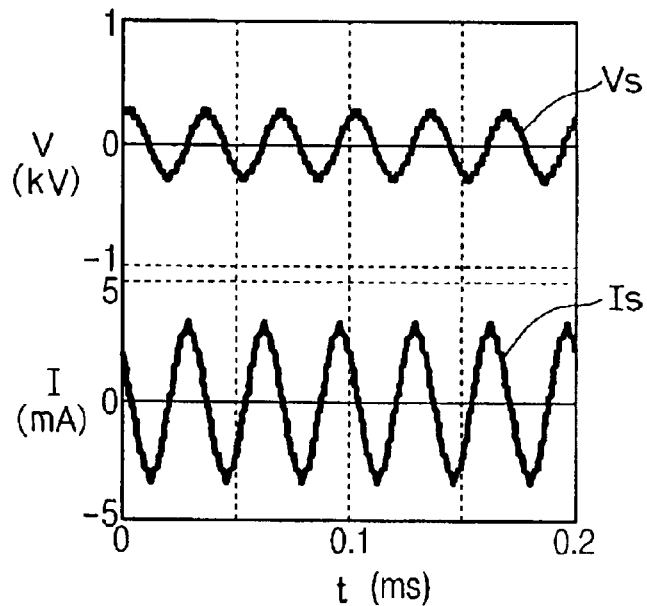
FIG. 4A is a schematic diagram showing another operation of the combustion condition detecting device according to the embodiment of the present invention.
Figure 4B:
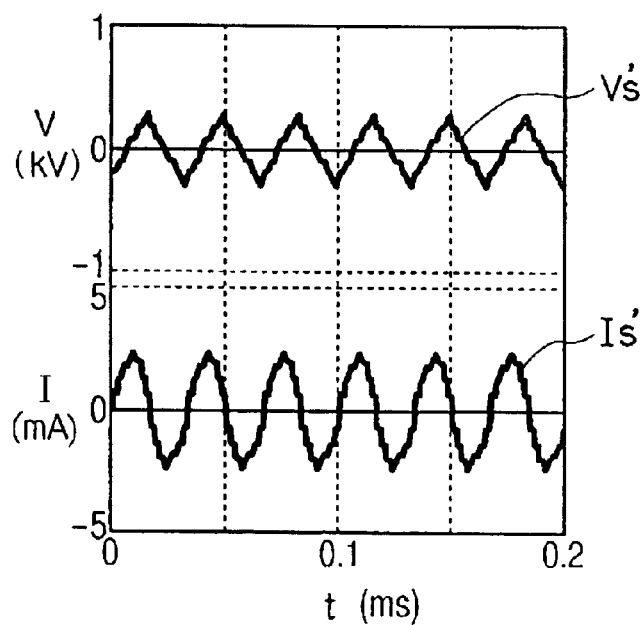
FIG. 4B is a schematic diagram showing an operation of a combustion condition detecting device to be compared with the combustion condition detecting device according to the embodiment of the present invention.

FIGS. 4A and 4B are based on results of experiments performed by the inventors. In FIG. 4A, $V_s$ represents a waveform of the secondary side voltage and $I_s$ represents a waveform of the secondary side current provided by the embodiment shown in FIG. 1 when no combustion ion exists between the opposing electrodes 11, 12. FIG. 4B shows a result provided by a comparative example, wherein the structure is similar to the embodiment of the present invention except that the structure does not have the capacitor 24. In FIG. 4B, $V_s'$ represents a waveform of a secondary side voltage and $I_s'$ represents a waveform of a secondary side current provided by the comparative example when no combustion ion exists between the opposing electrodes 11, 12. The waveform $V_s$ of the secondary side voltage shown in FIG. 4A is closer to a sine wave than the waveform $V_s'$ of the secondary voltage shown in FIG. 4B. Therefore, the embodiment can provide the secondary side current, the capacitive current, with a waveform $I_s$ closer to a sine wave than the comparative example can.

The current flowing between the opposing electrodes 11, 12 is a summation of the combustion ion current and the capacitive current, wherein the capacitive current increases and decreases independently of the quantity of the combustion ions between the opposing electrodes. Accordingly, the phases in which the current value equals to a predetermined value, "0" for instance, change in correspondence with the quantity of the combustion ions. Therefore, a system that detects such changes of the phases may be applied as a basic system of the combustion condition detecting device instead of the sample-and-hold circuit. The system detects phase differences relative to the standard phases in which the current value is "0" when the quantity of the combustion ions is null, for instance. In this case too, the phases in which the current value is "0" when the quantity of the combustion ion is "0" change because the current components with high order frequencies change due to the changes of the parts with time, and detection errors are produced. The system can be made highly accurate by disposing a capacitor therein like the embodiment.

The low pass filter is not limited to the capacitor if the low pass filter can eliminate the current components with frequencies higher than the applied frequency and can output an alternating current voltage close to a sine wave to the secondary winding of the transformer.

The present invention should not be limited to the disclosed embodiment, but may be implemented in many other ways without departing from the spirit of the invention.

What is claimed is:

1. A combustion condition detecting device for an internal combustion engine having a combustion chamber, the combustion condition detecting device comprising:
   a direct current source for supplying a direct current voltage;
   a pair of opposing electrodes disposed in the combustion chamber;
   a transformer having a primary side connected to the direct current source and a secondary side connected to the opposing electrodes, the transformer being turned on and off alternately to convert a direct current voltage of the battery to an alternating current voltage applied from the secondary side to the opposing electrodes to detect combustion ions existing between the opposing electrodes based on current signals corresponding to magnitude of current flowing between the opposing electrodes; and
   a low pass filter connected to the primary side of the transformer for eliminating current components having high order frequencies of the alternating current voltage so that a waveform of the alternating current voltage approximates a sine wave.

2. The combustion condition detecting device as in claim 1, wherein the low pass filter is constructed with a capacitor that discharges the current components having high order frequencies to a ground side.

3. The combustion condition detecting device as in claim 2, further comprising:
   a switching transistor connected in series with the direct current source and the primary side of the transformer and in parallel with the capacitor; and
   a driver circuit for turning on and off the switching transistor at a fixed frequency to apply the alternating current voltage following each ignition timing of the combustion chamber.

4. The combustion condition detecting device as in claim 1, wherein the opposing electrodes are electrodes of a spark plug that is mounted in the combustion chamber.

5. A combustion condition detecting method for an internal combustion engine having a transformer and a spark plug mounted in a combustion chamber, the method comprising steps of:

turning on and off, in each ignition timing in the combustion chamber, a transistor connected in series with a direct current source and a primary coil of the transformer to generate a high ignition voltage applied from a secondary coil of the transformer to a pair of electrodes of the spark plug;

continuing turning on and off of the transistor at a predetermined frequency, following the ignition timing, to generate an alternating current voltage applied from the secondary coil of the transformer to the pair of electrodes of the spark plug;

smoothing the alternating current voltage in a sine wave form by a capacitor connected in parallel with the transistor; and detecting an ion current flowing between the pair of electrodes of the spark plug by a resistor connected in series with the pair of electrodes and the secondary coil of the transformer.

* * * * *